United States Patent [19]
Hed

[11] Patent Number: 5,258,363
[45] Date of Patent: Nov. 2, 1993

[54] SUPERCONDUCTING INTEGRATING SPHERES

[75] Inventor: Aharon Z. Hed, Nashua, N.H.

[73] Assignee: Troy Investments Inc., Nashua, N.H.

[21] Appl. No.: 334,914

[22] Filed: Mar. 21, 1989

[51] Int. Cl.$^5$ .......................... G01J 1/04; H01B 12/00
[52] U.S. Cl. ............................. 505/1; 505/701; 505/780; 505/782; 505/783; 356/236; 250/228
[58] Field of Search ............... 505/1, 700, 701, 726, 505/780, 782, 783; 356/236; 250/228

[56] References Cited

U.S. PATENT DOCUMENTS

| | | | |
|---|---|---|---|
| 3,643,176 | 2/1972 | Gregory et al. | 372/44 |
| 3,661,686 | 5/1972 | Armstrong | 359/588 |
| 3,847,024 | 11/1974 | Beever et al. | 356/236 |
| 4,645,922 | 2/1987 | Welbourn et al. | 250/228 |
| 4,703,187 | 10/1987 | Hofling et al. | 250/228 |
| 4,764,003 | 8/1988 | Lake et al. | 350/600 |
| 4,886,776 | 12/1989 | Early et al. | 350/610 |
| 4,918,049 | 4/1990 | Cohn et al. | 505/701 |
| 4,925,830 | 5/1990 | Walsh | 505/1 |

FOREIGN PATENT DOCUMENTS 0006323 1/1989 Japan .................................. 505/701

OTHER PUBLICATIONS

Vries et al, "Preparation, Patterning, and Properties of Thin $YBA_2Cu_3O_{7-8}$ Films"; Appl. Phys. Lett. 52 (22); 30 May 1988; pp. 1904–1906.

Primary Examiner—Bruce Y. Arnold
Assistant Examiner—R. D. Shafer
Attorney, Agent, or Firm—Herbert Dubno

[57] ABSTRACT

A high efficiency integrating sphere that can be used in a large variety of scientific instruments. The sphere having an efficiency gain obtained by using a superconducting material, acting as a perfect reflector, on the inside hollow surface of the sphere. The sphere is operated with a delay between the incident and sensed light, heretofore not possible, and yielding substantial improvement in the signal-to noise ratio of the integrating sphere.

7 Claims, 2 Drawing Sheets

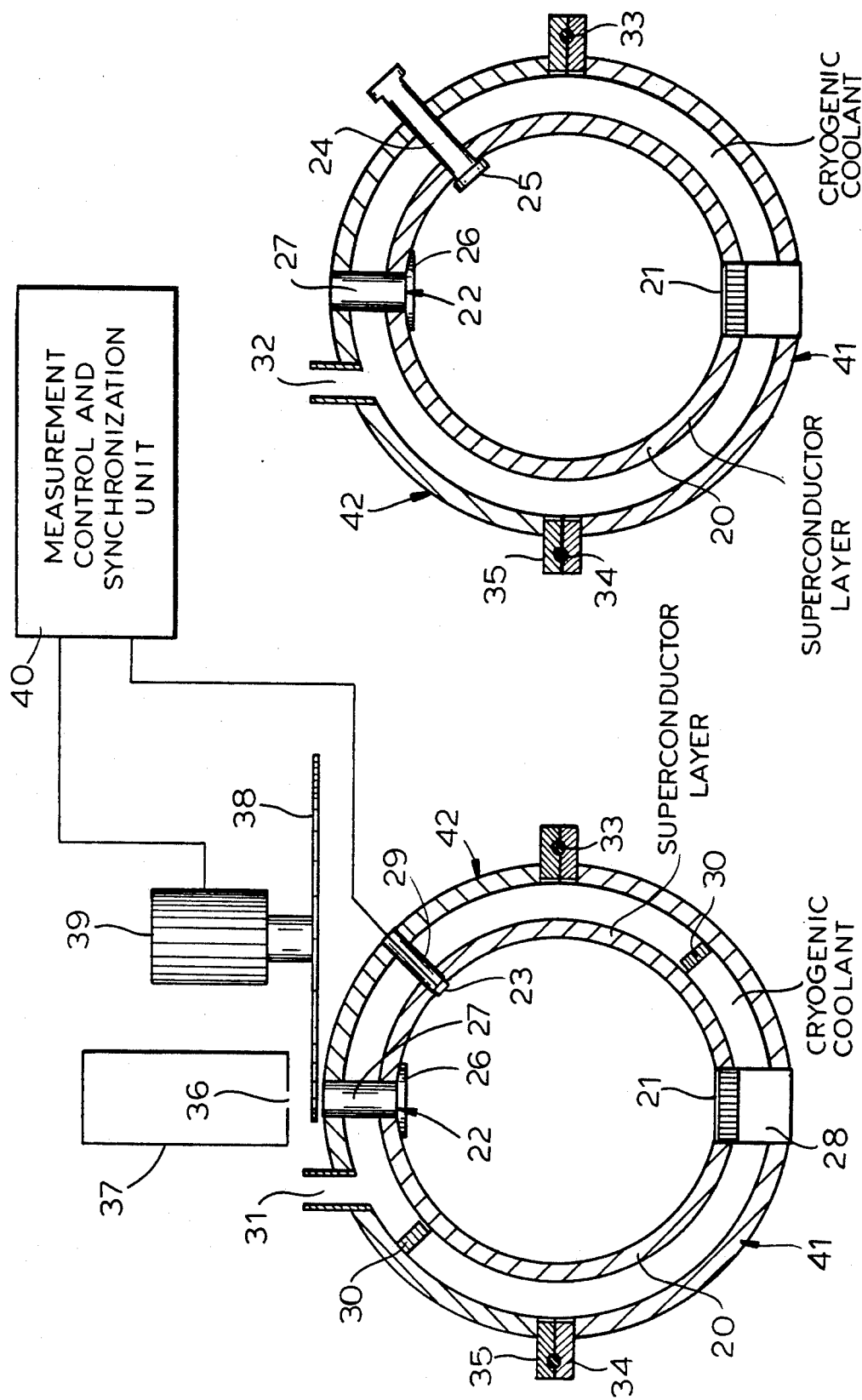

SUPERCONDUCTING INTEGRATING SPHERES

CROSS REFERENCE TO RELATED APPLICATION

This application is related to my co-pending application Ser. No. 07/292,469 filed on Dec. 30, 1988 entitled "Superconducting Mirrors."

FIELD OF THE INVENTION

My present invention relates to superconducting integrating spheres and, more particularly, high temperature superconductors, specifically as high reflectance coatings for scientific instruments using integrating spheres in the infrared part of the spectrum.

BACKGROUND OF THE INVENTION

In the design of a variety of optical analytical instruments, a device called an "integrating sphere" is often utilized. This device usually consists of a hollow sphere with the hollow coated with a highly reflecting substance. When handling the visible part of the spectrum, barium titanate or some zinc zirconates are often used, and when handling longer wavelengths, from the infrared to the microwave range, gold and other highly conducting metals can be used. In both cases it is usually preferred that the reflective surface be relatively rough, namely, are composed of small surfaces that are not all continuously change their orientations with the curvature of the substrate (like in a polished surface; this permits true diffusion of incident light on these surfaces and thus remove a high percentage of specularly reflected light that usually decreases the signal-to-noise ratio of such a sphere.

This can be achieved by a number of different pre-treatments of the substrates, all well known in the prior art of integrating spheres.

The efficiency of such integrating spheres is directly related to the reflectance of the coating of the hollow and, when optimization of signal-to-noise ratio is required, or there is to be maximization of recapture of illumination entering the sphere, a perfect reflector would be the most efficient inner coating of such an integrating sphere.

In my above-identified prior co-pending application entitled "Superconducting Mirrors" I have described the principles of making and using mirrors with extremely low losses, at least to wavelengths corresponding to the superconductor's band gap. In the same application I have mentioned that superconductors of the type (SC,I), (namely, the normal state is an semiconductor or a semimetal), could have band gaps large enough that reflection in the visible part of the spectrum may be made possible. This situation is postulated for materials where a virtual T(C) is much larger then the observed T(C).

OBJECTS OF THE INVENTION

It is an object of my invention to provide an integrating sphere in which losses of electromagnetic radiation within the sphere are drastically reduced by the use of a high temperature superconducting substance as the inner surface of said sphere. It is another object of this invention to provide a new application of high temperature superconductors as the reflecting element in integrating sphere. It is yet another object of this invention to provide a new technique of using integrating spheres whereby the light source illumination interval and the detection interval are separated in time to avoid direct sensing of the source by the detector.

SUMMARY OF THE INVENTION

According to the invention, an integrating sphere has a hollow coated with an appropriate superconductors, as described in the aforementioned application, particularly for optical scientific instrumentation. By replacing the classical gold and other metallic reflectors of the prior art with high temperature superconductors, I can obtain a sphere which redirects back onto a sensor the great majority of the light that entered the sphere, thus increasing the ability of the sphere to act as an optical integrator without losses. One of the results of this feature is that it is now possible (within the wavelength limitations set forth) to capture light within such a sphere for a short but finite time period, without having said light being completely absorbed by the reflector. This feature thus allows for the illumination of a sample with a short pulse of light, and sensing the extent of such sample's interaction (in the reflection mode) with such light without having the original beam being sensed simultaneously. This greatly increases the signal-to-noise ratio of reflective spectroscopical analysis.

BRIEF DESCRIPTION OF THE DRAWING

The above objects, features and advantages of my invention will become more readily apparent from the following description, reference being made to the accompanying drawing in which:

FIGS. 2 and 3 are two sections through a sphere according to an example herein taken in perpendicular planes.

DESCRIPTION OF THE INVENTION

Figure 1:
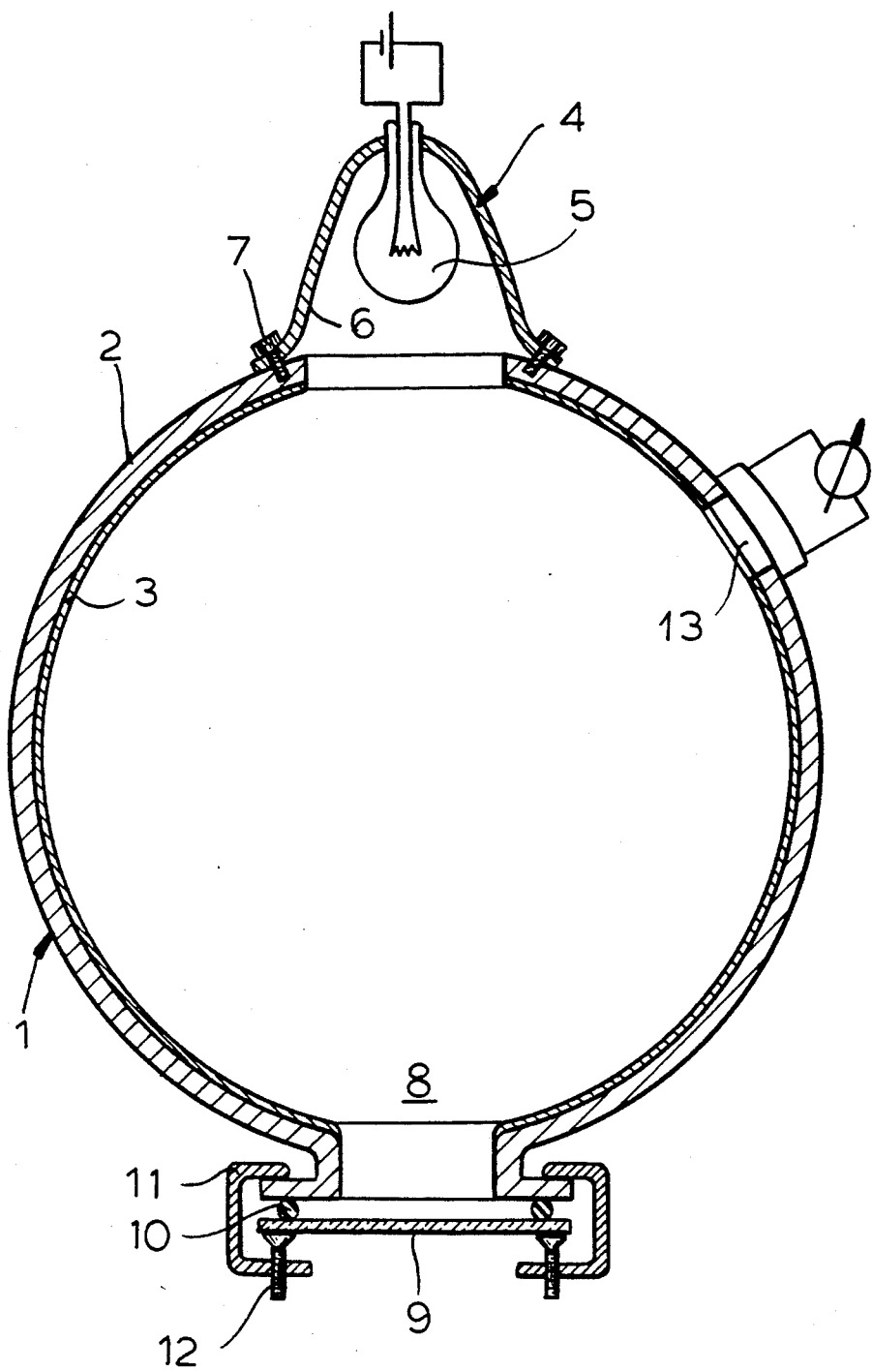
FIG. 1 is a cross sectional view through an instrumentation integrating sphere of the invention.

In the following description of the invention, the new devices will be described independently of the wavelengths of the electromagnetic radiation involved. It should be understood, however, that the applicable wavelengths are limited on the short side (high energy per photon) by the band gap, or the binding energy of the superconducting charge-carrier pairs of the superconductor used as the integrating sphere reflecting medium, and on the long side (low energy photons) of the spectrum, by the dimensions of the cavities.

In FIG. 1 we show a cross section through a typical instrumentation integrating sphere 1. The shall 2 can be made from any appropriate material on which the superconducting layer 3 can be deposited. If the sphere must be operated at cryogenic temperatures, the shell itself can be double walled to form an appropriate dewar for the cooling liquid. The inner wall of such a dewar, which is also the substrate for the superconducting layer, is made of a material that conducts residual heat generated in the sphere to the cooling liquid. Such a substrate can be made for instance, from copper, or sometimes, copper coated with a thin diamond-like carbon layer. The outer wall of such a dewar can be made of thermally insulating materials well known in the prior cryogenic art. An example can be stainless steel enclosed within a polystyrene foam. The inner surface of the sphere prior to the deposition or application of the superconducting layer should be treated to obtain appropriate roughness, by techniques well known in the prior art of integrating spheres.

The superconducting layer should have a minimal thickness that exceeds the penetration depth of magnetic fields to assure maximum reflection of electromagnetic radiation from the superconducting surfaces. In the part of the spectrum where the superconductor is reflecting, one can expect the reflectance losses to be at least 4 orders of magnitude lower than that of an equivalent gold reflector.

The sphere can be made from a single cast element, or assembled from two halves, depending on the best manufacturing and assembly technique for the specific application. The sphere has an opening where the light source assembly (4) can be fastened. The design of the light source 5 should be closely related to the unique properties of the superconducting coating chosen and of course the intended application.

In FIG. 1, it is assumed that the light source or bulb 5 is treated to provide the matching between the spectrum of light intended for the application and the properties of the superconductor layer. For instance, if the absorption limit of the superconductor is at 20 microns, the sphere should be used only for applications requiring wavelengths greater than 20 microns. In this case, the outer or inner surface of the bulb, should be coated with an optical filter (a variety of which are well known in prior art, for instance dichroic interference filters), reflecting back onto the heating element all light with wavelengths shorter than 20 microns and transmitting light with wavelengths longer than 20 microns, or a far infrared cut off filter. Such filters that are up to 80% efficient are well known.

The light bulb itself is seated in an appropriate reflector 6, which is itself a superconducting coating on a surface whose form could for instance be a paraboloid of revolution with its focal point corresponding as much as possible with the heating element in the light bulb. The reflector is fastened to the sphere with appropriate fasteners 7, and an "O" ring (not shown in the figure) can be used to seal the sphere from external influences and leaks. The parabolic structure of the reflector 6 would optimize the illumination through the aperture 8 of the sample being examined by the instrument (not shown).

The aperture 8 is equipped with an optical window 9, made of a material transparent to the electromagnetic radiation spectrum intended (as in the example cited above, wavelength longer than 20 microns) allowing illumination of a sample below the transparent optical element or window. The window is fastened against an "O" ring 10, for instance with brackets 11 and pressure screws 12.

It should be clear to persons familiar with the standard design of optical instruments that the windows and means for attaching them to the integrating sphere can take a number of variant forms. For instance, the window can be coated with an antireflective coating, the fastening can be achieved by keeping a dynamic vacuum inside the sphere, or by many other fastening techniques.

The light that impinges on the sample interacts with the sample, part being absorbed. The light reflected back into the integrating sphere, carries a signature (where light was absorbed by the sample) which is related to the nature of the sample. This light is analyzed by the sensor 13 which constitutes means cooperating with the spherical inner surface for collecting a light signal therefrom.

The sensor, whose structure and operation are part of the prior art, can be equipped with an appropriate set of filters to measure the intensity of the incoming light only at given wave lengths. It should be clear to persons familiar in the art of designing such optical systems that the filters (or a filter wheel) could also be positioned in front of the source, and using synchronization techniques between the filter drive with the sensor output, can determine the appropriate distribution of back reflected light at different wavelengths.

The advantage of a superconducting mirror in this application is obvious. The light reflected back from the sample, is reflected onto the inner surface of the integrating sphere, and only a small proportion of this reflected light is detected directly by the sensor (in the first pass no more than the ratio of the sensor's aperture to the sphere inner surface. With a very good gold reflecting surface the best reflection one usually can expect is 99%, namely 1% of the light is absorbed by the gold. (If the gold layer is extremely thin, in the order of 100 angstrom, some light can be transmitted and can be absorbed by the support structure. This depends strongly on the wavelength of the illumination.) The balance of the light reaches the sensor after multiple reflections. One can calculate that a light beam that has been reflected 100 times within such a sphere would in the case of a reflector with 99% reflectance have only 36% of its original intensity, while with a superconducting reflector, only four orders of magnitude better than gold (still a poor quality superconducting reflector) the beam intensity will still be 99.99% of the original beam. Thus with a superconducting reflector, the efficiency of collecting light from a sample is much greater and thus a major improvement in instrument operation can be gained by using an integrating sphere that is coated with superconductors.

Furthermore, new methods of operation of the integrated sphere can be considered as well. For instance, one of the sources of degradation of the signal-to-noise ratio in current instruments, is rooted in the fact that a large portion of the light incident on the sensor has never interacted with the sample, but is reflected from the sphere and the sample window directly or only after few reflections, onto the sensor. In the instant invention I can eliminate or at least lower the proportion of uninteracted light in the sensed beam, by allowing for a time delay between the illumination and the sensing. This principle of the instant invention can be implemented in numerous ways. One such implementation is by positioning in front of the sensor a rotating wheel with a superconductor coating facing the hollow of the sphere (or an absorbing medium if gaining additional reflected light from the sample is not critical) which rotation is synchronized with that of the filter wheel (in front of the light source), but delayed by 100 nanoseconds. In a sphere of about 4 cm in diameter, the average distance traveled by the beams between reflections is (for ease of calculation) 3 cm. Then in a 100 nanosecond period the light within the sphere would have been reflected 1000 times, and thus contain a very small proportion of uninteracted light.

This technique is completely new to the art. If one attempts such a delay design with a gold coated integrated sphere, only 0.0043% of the original beam energy would be left. This energy is too small of a signal (taking into account other source of losses) to detect. With the superconductor described here, however, still 99.9% of the light is being reflected, thus allowing a measurable signal.

In order to use such a delay technique, one should coat the nonfilter part of the filter wheel with the superconducting surface to avoid excessive losses.

In the co-pending application entitled "Superconducting Mirrors" mentioned above, I recommend use of a protective surface on the superconductor to avoid interaction with the environment. In this invention such a surface is not always required. For instance if the hollow is always under vacuum, one can avoid deterioration of the surface from the elements. Furthermore, new superconducting materials are being developed with less propensity to interact with the environment. Nevertheless, if a protective layer is deemed to be required, one should chose an appropriate semiconducting or insulating substance with a band gap larger than that corresponding to the cut off wave length of the integrating sphere, and with such purity that absorption in the protective surface is minimized.

Such coating materials, both amorphous and crystalline are known in the prior art and extensively used in electrooptical devices, particularly in optical fibers, where losses are minimized even after many miles. If a coating is 100 Angstrom thick, 1000 reflections through such a coating would be equivalent to the loss through 20 microns of such a transparent.

DISCUSSION AND APPLICATIONS

In the present disclosure, we have shown how an integrating sphere coated inside with a superconducting substance can be used as a high efficiency device in many scientific instruments.

Example of instruments that could use this new device will change as new superconductor with shorter wavelength cutoff are discovered, and will eventually include reflection spectrometer, atomic absorption spectrometer, near infrared reflectance analysis systems, Ramman spectrometers, color analyzers and integrators, moisture detectors, a number of medical diagnostic reflectance analyzers and many other systems using high reflectance integrating spheres.

A particularly important application for such an integrating spheres are as infrared calibrating standards and black body measurements.

With the current generation of high temperature superconductors, we can reach cutoff wavelengths of about 20 microns (123 superconductor at 77 K.).

We have also shown how integrating spheres can be used in new delay modes between the illumination and measurement to allow for further improved signal to noise ratio of these systems.

SPECIFIC EXAMPLE

A Ramman reflecting spectrometer, is a particularly good example of the latter application. For Ramman spectroscopy, cryogenic detectors should be used anyhow, and thus the requirement of having a cryogenic integrating sphere is not demanding. The wavelengths involved are in the far infrared, which are longer than 20 microns.

A sphere 20 (FIGS. 2 and 3) 30 cm in inside diameter is manufactured from two spun hemispheres (stainless steel) welded together. The large diameter allows for increasing the delay time to 1 microsecond. A sample aperture 21 of 2" and a light source aperture 22 of 1" opposing each other on a major diameter are pierced in the sphere. The sensor aperture 23 is only $\frac{3}{4}$" in diameter and at 45° from the light source. The sample aperture was made that large to allow deposition of the superconductor inside the sphere without having to resort to halving the sphere. An additional $\frac{1}{2}$" aperture 24 is pierced in a plane orthogonal to the prior three apertures, this opening is to allow evacuation. A flat circular piece 25 of stainless steel is spot welded in front and about 1 mm inside the sphere with the help of three stubs bent from the disk. This baffle screens the evacuation opening and becomes coated with the superconductor in the deposition process described below, thus reducing potential losses to the evacuation opening. An additional baffle 26 precoated with the 123 superconductor with a central slit 2 mm×5 mm is spot welded at the source aperture to prevent excessive optical losses there (our the source is a slit 1 mm×3 mm as will be seen below).

On each aperture a short cylindrical stub 27, 28, 29 about 1.25" long terminated with a vacuum flange is welded as well. Prior to deposition of the superconductor, six support elements 30 $\frac{3}{8}$" in diameter and $\frac{1}{4}$" long are cemented to the outside surface of the sphere (on the two circles perpendicular to the major diameter connecting the source aperture and the sample aperture and at 45° to that diameter, each at the apex of equilateral triangles offset from one another by 180°). These stubs are made of polyurethane and help in positioning the external sphere.

The 123 superconductor is coated onto the inside of the inner sphere by the technique described in the co-pending application entitled "Superconducting Mirrors" except that the sphere is continuously rotated around the target and slow translational movement back and forth of the sphere relative to the target is also executed. As a result of this deposition, the surface of the 1,2,3 compound is quite diffuse naturally (apparently due to the continuous interruption of growth at any given location due to the combined rotation and translation of the sphere).

This sphere is now enclosed within two hemisphere 41, 42 with appropriate openings mating the four opening on the inner sphere, and having an additional two opening 31 and 32 feeding the space between the inner sphere and the outer sphere, into which a cryogenic liquid (liquid nitrogen) can be fed. The two hemisphere are sealed together with an "O" ring 33 pressed between two flanges 34, 35 at a major circle perpendicular to the diameter connecting the sample and source apertures.

The three optical apertures are sealed by placing far infrared transmitting crystals against their respective "O" rings and flanges.

The sensor is a Cd-Hg-Te infrared sensor (liquid nitrogen cooled).

The source is the output slit 36 of a far infrared spectrometer 37 (the wave length can be varied between 20 to 40 microns) in front of which a chopper wheel 38 of 16 cm in radius having six equidistant slits can be rotated. The slits are 1 mm in width and 3 mm long with their center at 15 cm from the center of the chopper wheel and their long dimension radial.

The motor 39 for the chopper wheel is capable of rotating at 60,000 rpm. When the chopper is rotating at full speed, each millisecond, 6 short light pulses about 1.5 microseconds long are allowed in the sphere separated from each other by about 150 microseconds. (Because of its high sensitivity, the recovery time of the sensor is quite slow, at about 100 microseconds).

The bias of the sensor is electronically adjusted (through a synchronizing circuit 40) to sense only input which is about 1 microsecond after the illumination of the sphere. This integrating sphere provides the time delay required between the illumination and detection of reflection from the sample.

It is understood that the above described embodiments of the invention are illustrative only and modifications and alterations thereof may occur to those skilled in the art. Accordingly, it is desired that this invention not be limited to the embodiments disclosed herein but is to be limited only as defined by the appended claims.

I claim:

1. An integrating sphere comprising a hollow body having a spherical inner surface coated with a roughened layer of a high temperature superconductor producing diffuse reflection and means cooperating with said surface for collecting a light signal therefrom.

2. The integrating sphere defined in claim 1, further comprising a detector aperture, light source aperture and a detector and light source juxtaposed with the respective apertures and a superconductor coated baffle in an optical path between the detector and the light source.

3. The integrating sphere defined in claim 2, further comprising an additional aperture for sample exposure.

4. An apparatus as defined in claim 3, further comprising means operatively connected with said light source for starting and stopping the light source, means operatively connected to said detector source for starting and stopping the detector, and means for introducing a controlled delay between a start of illumination and a start of the detection of flux from the integrating sphere, the means for starting and stopping the light source being a variable high speed chopper wheel, having slits of such dimensions and spacing so as to achieve the desired timing of the illumination.

5. An apparatus as defined in claim 4, further comprising electronic means for gating synchronously the detector to the light source.

6. An apparatus as described in claim 4 wherein the superconductor coating is essentially an $YBa_2Cu_3O_{7-x}$ compound having a layer thickness of at least 1000 angstrom.

7. An apparatus as defined in claim 4, wherein the superconductor coating is made of bismuth or a thallium containing oxide superconductor.

* * * * *